United States Patent [19]

Collier

[11] Patent Number: 4,911,720
[45] Date of Patent: Mar. 27, 1990

[54] PARTICULAR SURFACE REPLACEMENT PROSTHESIS

[76] Inventor: John P. Collier, Box A-63, Hanover, N.H. 03755

[21] Appl. No.: 474,179

[22] Filed: Mar. 10, 1983

[51] Int. Cl.$^4$ ............................................... A61F 2/30
[52] U.S. Cl. ............................................................ 623/16
[58] Field of Search ..................... 3/1.5, 1.51, 1.912, 3/1.913, 1.911; 128/92 C, 92 CA

[56] References Cited

U.S. PATENT DOCUMENTS

| | | | |
|---|---|---|---|
| 3,808,606 | 5/1974 | Tronzo | 3/1.5 |
| 4,000,525 | 1/1977 | Klawitter | 3/1.511 |
| 4,156,943 | 6/1979 | Collier | 3/1.5 |
| 4,546,500 | 10/1985 | Bell | 623/1 |

Primary Examiner—Richard J. Apley
Assistant Examiner—David J. Isabella
Attorney, Agent, or Firm—Robert Shaw

[57] ABSTRACT

An articular surface prosthesis composed of a porous material that is substantially noncorrodible and nonbiodegradible by body fluids. The prosthesis serves as a replacement of, for example, a femoral cap. The prosthesis fits over the femur which is shaped, typically, to a right circular cylinder outline, to receive the replacement which has a similarly shaped cavity. The prosthesis fits snugly over the femur and presents at the bone prosthesis interface coarse pores (e.g., 100 to 500 micrometers) to permit bone ingrowth; the pores are graded toward smaller or fine sizes (e.g., <50 micrometers) to prevent bone ingrowth and permit cartilage ingrowth at the articulating side of the prosthesis.

18 Claims, 1 Drawing Sheet

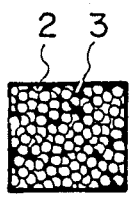
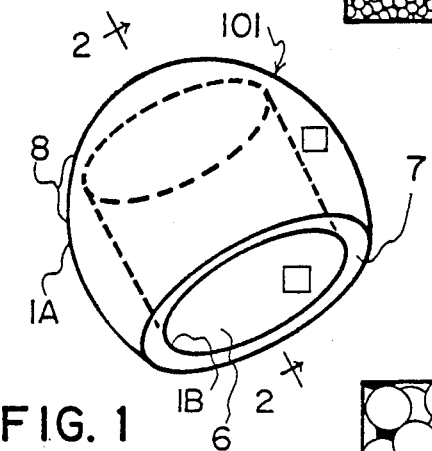
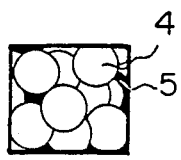
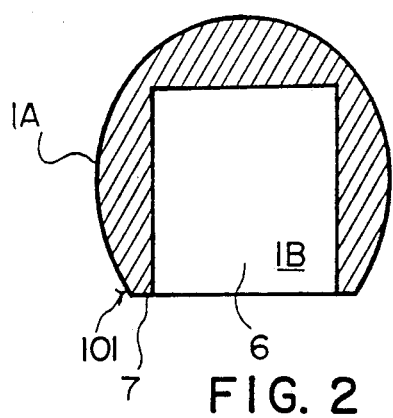
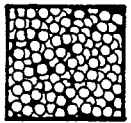
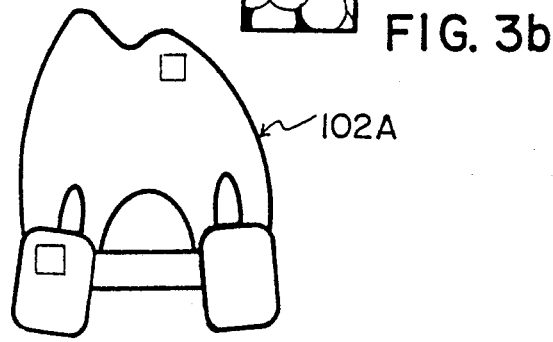
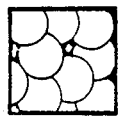
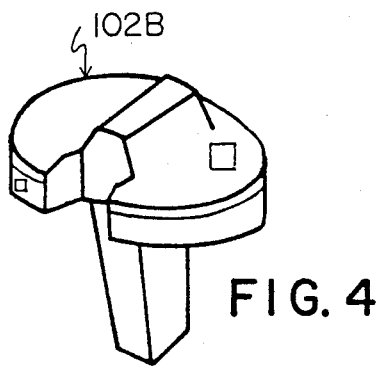
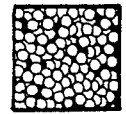

PARTICULAR SURFACE REPLACEMENT PROSTHESIS

The present invention relates to articular surface replacement prostheses.

Attention is called to United States Letters Pat. 4,156,943 (Collier, the present inventor) and the art of record therein, as well as United States Letters Pat. 4,081,866 (Upshall et al.); 4,159,895 (Frosch et al.); 4,187,559 (Grell et al.); 4,194,250 (Walker); 4,206,516 (Pilliar); 4,223,412 (Aoyagi et al.); 4,307,472 (Morris); 4,314,380 (Miyata et al.); 4,222,128 (Tomonago et al.).

The invention herein addresses the continuing problem of providing prostheses to replace injured or defective articular structures and surfaces thereof. Among the difficulties in any such replacement is that of achieving secure attachment to a bone at one side of the prosthesis at an articular surface while nevertheless achieving a low-friction sliding surface at the other or obverse side thereof, particularly since the two characteristics needed to perform the necessary functions are mutually antagonistic. Joints in the human body that often require replacements of the type herein disclosed include the hip, the knee, the shoulder, the ankle, and others.

There are several styles of surface replacements available for use today. Among these are the Tharies- and the T.A.R.A.-style devices. The prime difference between the two is that the T.A.R.A. has a thin stem for alignment purposes whereas the Tharies does not. The T.A.R.A. was designed by Dr. Charles Townley and has been in clinical use since 1952. Both designs have been shown to have clinical efficacy but both have limitations. Both devices are very sensitive to surgical technique. If either surface replacement is implanted so that it is loose at the onset, then this looseness between the surface replacement and the bone will cause the formation of a granulation tissue which will slowly eat away the interface until there is no bone left and the surface replacement becomes detached. Loosening is highly probable with these inplant designs because the inside of the surface replacements are smooth and rely on an interference fit between the smooth metal component and bone for fixation. While such devices are presently designed as surface replacements at the femoral side of the hip, the concept can also be applied to the femoral side of the knee, the tibial side of the knee and potentially the acetabular side of the hip. It may also be used potentially in the elbow, the wrist, the ankle, the shoulder, and so forth. Accordingly, it is a principal object of the present invention to provide an articular surface replacement which will not loosen with time and which will provide a nominally friction-free surface at the joint.

It has been well documented by the inventor that clinically bone will grow into the porous metal coating of femoral hip prosthesis stems when the stems have been well fixed in the femoral medullary canal and the pore size is 100 microns or greater. A pore size of 150 to 500 microns appears to be ideal for vascularized bone ingrowth. Further, with the use of the porous coated prosthesis, it has been clinically demonstrated by the present inventor, that bone will grow into the porous surface and that the mechanical interlocking thereby generated between the bone and the implant will keep it from loosening. It is, then, an object of this invention to take the technique of bone ingrowth of a porous surface and apply it to surface replacement.

According to the present teaching, the surface next to bone should have interconnecting pores between about 150 and 500 microns in diameter to permit bone ingrowth but there needs to be a gradation of pores from the side opposed to bone to the side opposed to the articulating surface such that bone can grow only partially into the porous surface but not all the way through because the pores at the articulating side are too small. Bone has not been found growing into pores of less than 50 microns under clinical conditions. It has been demonstrated for present purposes that cartilage will grow into pores as small as 10 to 20 microns in diameter; it is, as later discussed in some detail, the smaller pores at the articulating surface of the inplant upon which cartilage is grown. This very fine-pored articulating surface will be a home for the cartilage and will provide a matrix for it to grow into as well as a reservoir for the fluids necessary to give it needed nutrients.

A further object, therefore, is to provide an articular surface replacement prosthesis.

Another object is to provide a prosthesis which can be secured to a bone in a human as a replacement and yet provide a low-friction sliding surface.

These and still further objects are addressed hereinafter.

The foregoing objects are achieved, generally, in a porous articular surface replacement prosthesis composed of a porous material that is substantially noncorrodible and nonbiodegradable by body fluids; the porous material comprises a plurality of particles of the material fused together at points of contact with each other to define a plurality of connected, interstitial pores distributed throughout the porous material, the average interstitial pore size of said material being graded from large or coarse at the side thereof in contact with bone upon implantation to much smaller or fine pores at the articulating surface side thereof upon installation. In preferred form, the articulating surface side has a pregrown cartilage layer disposed over the prosthesis at the articulating surface side thereof.

The invention is hereinafter described with reference to the accompanying drawing in which:

FIG. 1 is an isometric view of a femoral cap prosthesis according to the present teachings, a prosthesis having graded pore size;

FIG. 1a is a magnification of the small square area in FIG. 1 to which it is adjacent;

FIG. 1b is a magnification of the small square area in FIG. 1 to which it is adjacent;

FIG. 2 is a section view taken upon the line 2—2 in FIG. 1 looking in the direction of the arrows;

FIG. 3 is an isometric view of a femoral knee prosthesis;

FIG. 3a is a magnification of the small square area in FIG. 3 to which it is adjacent;

FIG. 3b is a magnification of the small square area in FIG. 3 to which it is adjacent;

FIG. 4 is an isometric view of a tibial knee prosthesis;

FIG. 4a is a magnification of the small square area in FIG. 4 to which it is adjacent;

FIG. 4b is a magnification of the small square area in FIG. 4 to which it is adjacent;

The present invention, as above indicated, has application in a number of parts of the body at which a prosthesis is needed to replace an articulating member. When the replacement is at a joint at which the prosthesis forms an interface between a bone and a sliding surface, the prosthesis, according to the present teachings, is a porous implant having a gradation of pore size from fine at the articulating surface side to coarse at the bone interface. The fine pore size (i.e., average of about 50 micrometers or less) prevents bone ingrowth while permitting cartilage ingrowth; the coarse pore size (i.e., from about average size of about 100 to 500 micrometers) permits bone ingrowth and hence a secure bond between the bone and the implant. In one embodiment, host cartilage cells grow into the porous surface in culture (in vitro) and later are implanted. The cartilage surface grown on the prosthesis will perform its normal function of lubricating the sliding, articulating surface. To simplify the explanation below greatest emphasis is placed on the invention in the context of a femoral hip component of the type shown at 101 in FIGS. 1 and 2, but the invention, as indicated, is broader in context.

The implant 101 is a totally porous articular surface prosthesis composed substantially entirely of a porous metallic material that is substantially nonbiodegradable by body fluids; the prosthesis 101 may be formed of Vitallium metal powders (e.g., F-75 cobalt-based alloy) sintered in a nonoxidizing environment at a temperature within about 25° C. of the melting point of the powders for a period of from a few minutes to about one hour so as to fuse particles of the powder together at points of contact with each other. Typically the time is in the range from fifteen minutes to about an hour. The temperature and sintering time must be kept below respective values at which the powders would fuse to form a nonporous solid but both must be adequate to provide the strengths needed to withstand the stresses applied on the prosthetic implant.

In accordance with the present teaching, the pore size is graded from a fine interstitial average pore at the articulating surface side labeled 1A in FIGS. 1 and 2 to a coarse interstitial average pore size at the side thereof in contact with bone upon implantation. This graded facet is shown as a magnification in FIG. 1a wherein the label 2 indicates metal particles and 3 indicates fine interstitial pores at the outer (articulating surface) side of the prosthesis 101; the label 4 in the magnification of FIG. 1b indicates metal particles that are relatively large (compared to the prothesis 2) and label 5 indicates coarse interstitial pores of the bone interface of the prosthesis 101.

The same arrangement of magnifications is used for FIGS. 3 and 4, the labels 1-5 being unnecessary.

Preparation of the femur for installation of the prosthesis 101 is typically made by use of a cutting tool that forms the bone in the shape of a cylinder whose outer dimensions correspond closely to the inner dimensions of the cylindrical cavity labeled 6 in FIGS. 1 and 2. Very quickly after implantation, bone growth occurs radially outward from the bone and into the walls shown at 1B of the cavity 6. To place some perspective on the present concepts, the lip labeled 7 of the prosthesis 101 is typically one to five millimeters which is also about the range of thicknesses of the prosthesis.

The prosthesis 101 is a femoral cap. It may be installed on a properly prepared femur stub without further measures or it may be threaded onto a stem which will aid in guiding it in accordance with presently available techniques; see the Collier patent for greater details.

A short discussion follows giving techniques for forming the prosthesis. The porous articulating surface prosthesis can be made by a number of methods. For example, a powder of varying diameters can be formed in a mold, pressed to shape with a binder and then sintered in a furnace. Alternatively, blocks of powder can be sintered very lightly in the furnace to make a green compact which then can be machined, pressed, and resintered to final size. (See the Collier patent for a more detailed discussion.) Typically powders in the range between about 80-325 mesh are used at the articulating surface side of the prosthesis and powder between 60-80 mesh at the bone ingrowth side of the prosthesis. It is quite likely that the articulating surface of the prosthesis will need to be ground in order to make a surface smooth enough to have very low friction. The grinding needs to be done very slowly and with a lubricant so as not to smear metal into the pores thereby closing them.

The prosthesis 101 may have a thin layer 8 of cartilage (FIG. 1) covering all or most of the articulating surface 1A, the layer of cartilage being deposited prior to installation. The cartilage can be grown by in vitro culturing using autographed cartilage taken from the person who will receive the implant. The cartilage thickness typically will be many cell layers thick and is ideally about one millimeter thick. A description of culturing chondrocytes now follows.

To culture chondrocytes, it is necessary for a culture of several cells to be taken from the host and then they can be cultured, in vitro, using the equivalent of bovine calf serum as a nutrient medium. The cells can be grown onto the porous articulating surface and, given time, will provide a uniform layer over the articulating surface. Once a secure, intact satisfactory layer of chondrocytes has laid down as a cartilage matrix over the surface of the articular replacement, the articular replacement can then be implanted into the body just as a device without the cartilage surface would be.

A femoral knee prosthesis is shown at 102A in FIG. 3 and a tibial knee prosthesis is shown at 102B in FIG. 4. Again the pore size gradation discussed above is employed.

Other powders than Vitallium can be used to fabricate the prostheses 101, 102A and 102B, such as, for example, the titanium-aluminum-vanadium alloy, Ti-6A14V. Any material used, metallic or other, must be one that will not cause inflamation or otherwise effect deterioration of the body, upon installation. And, further, it must be noncorrodable and nonbiodegradable by body fluids. The implant ideally is totally porous (i.e., interconnected interstitial pores) for the purposes above discussed, but also to permit body fluids to permeate the system. For purposes of bone and cartilage ingrowth, it is necessary that a substantial faction of the respective surface be porous, but porosity to a depth of about 200 to 500 micrometers will usually suffice for that purpose. The discrete powders particles, in any event, are prepared in a compact wherein they are fused at points of contact by being heated to a temperature near to but slightly below the melting temperature for a time period adequate to effect fusion at the points of contact but not so long that complete melting and solid formation will occur. The prosthesis thus formed must be strong enough (e.g., have fatigue strength of at least about 10,000 psi and yield strength of at least about 20,000 psi, both in compression) to withstand the large impact forces encountered upon installation. The Collier patent and further cited art may be used to augment this specification in terms of metallurgical forming techniques.

Further modifications of the invention herein disclosed will occur to persons skilled in the art and all such modifications are deemed to be within the scope of the invention as defined by the appended claims.

What is claimed is:

1. A strong, totally porous articular surface replacement prosthesis composed substantially throughout of a porous metallic biomaterial, said porous material comprising a plurality of particles of said metallic material fused together at points of contact with each other to define a plurality of connected, interstitial pores distributed throughout the porous metallic material, the average interconnecting pore size of said material being graded from about 100 to 500 micrometers at the side thereof in contact with bone upon implantation and to about 50 micrometers or less at the articulating surface side thereof upon installation.

2. A prosthesis according to claim 1 in which the particles comprise many small, discrete, generally ball-shaped particles of the metallic material bonded together at their points of contact with each other to define a large number of connected interstitial pores substantially uniformly distributed through the porous metallic material but graded in size from the side of the prosthesis opposed to bone downwardly in size toward the articulating surface side thereof.

3. A prosthesis according to claim 1 in the form of a porous interconnected structure having a fatigue strength in compresion greater than at least about 5,000 psi and a yield strength in compression of at least about 10,000 psi.

4. A prosthesis according to claim 1 wherein a substantial fraction of the prosthesis comprises pores graded from coarse at the bone side thereof to fine at the articulating surface side thereof.

5. A prosthesis according to claim 1 in which the pores at both the bone side thereof and the articulating surface side thereof interconnect with one another so that, when the prosthesis is implanted, bone growth into the bone side and cartilage growth into the articulating surface side thereof can occur and nutrients can flow to the cartilage.

6. A prosthesis according to claim 5 having cartilage grown thereon, in vitro, at the articulating surface side prior to implantation of the prosthesis.

7. A prosthesis as claimed in claim 1 in which the bonds between the particles at said points of contact are formed of the particle material so that the porous material is in the form of a unitary structure wherein the material thereof is substantially the same composition throughout the structure and including the bonds, said pores being distributed substantially uniformly throughout the prosthesis, but in a graded configuration, pores in the interior of the prosthesis being in communication with pores at and near the surface thereof.

8. A prosthesis as claimed in claim 1 in which the porosity is between about 10 and 40 percent.

9. A prosthesis as claimed in claim 1 having cartilage grown upon the articulating surface side thereof, which cartilage is grown, in vitro, in a culture from cells taken from the host, the pores being interconnected to permit nutrients to flow to the cartilage when the prosthesis has been implanted.

10. A porous articular surface replacement prosthesis a substantial fraction of which is a porous biomaterial, said porous material comprising a plurality of particles of said material fused together at points of contact with each other to define a plurality of connected, interstitial pores distributed through most of the porous prosthesis, the average interstitial pore size of said material being about 100 to 500 micrometers at the side thereof in contact with bone upon implantation and about 50 micrometers or less at the articulating surface side thereof upon installation.

11. A prosthesis according to claim 10 which, prior to implantation, has a cartilage layer of living cells disposed over the articulating surface side thereof.

12. A porous articular surface replacement prosthesis composed of a porous biomaterial, said porous material comprising a plurality of particles of said material fused together at points of contact with each other to define a plurality of connected, interstitial pores distributed within the said prosthesis, the average interstitial pore size of said pores being coarse at the side of the prosthesis in contact with bone upon implantation to permit bone ingrowth therein and fine enough at the articulating surface side thereof upon installation to prevent bone ingrowth into the articulating surface side, but sufficiently large to permit cartilage ingrowth therein.

13. A prosthesis according to claim 12 having a thin layer of cartilage covering all or most of the articulating surface side, 14. A prosthesis according to claim 12 in which the porosity at both sides of the prosthesis extends inwardly at least to a depth of about 200 micrometers.

15. A prosthesis according to claim 14 in which the pores interconnect from one side thereof to the other side thereof.

16. A prosthesis according to claim 1 having cartilage disposed at the articulating surface side thereof.

17. A prosthesis according to claim 1 having living cartilage at the articulating surface side thereof prior to implantation.

18. A prosthesis according to claim 1 wherein the pore size at the articulating surface is in the range from 10 to less than 50 micrometers to permit cartilage growth at the articulating but small enough to prevent bone ingrowth to the articulating surface.

* * * * *